US009204991B1

(12) United States Patent
Harkins

(10) Patent No.: US 9,204,991 B1
(45) Date of Patent: *Dec. 8, 2015

(54) MANDIBULAR ADVANCEMENT DEVICE

(71) Applicant: Stephen J. Harkins, Tucson, AZ (US)

(72) Inventor: Stephen J. Harkins, Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/536,115

(22) Filed: Nov. 7, 2014

Related U.S. Application Data

(63) Continuation-in-part of application No. 13/468,766, filed on May 10, 2012, now Pat. No. 8,881,733.

(60) Provisional application No. 61/487,588, filed on May 18, 2011.

(51) Int. Cl.
*A61F 5/56* (2006.01)

(52) U.S. Cl.
CPC .................................. *A61F 5/566* (2013.01)

(58) Field of Classification Search
CPC ......... A61F 5/566; A61C 5/14; A63B 71/085
USPC ......... 128/848, 859–862; 602/902; 433/6, 19, 433/37, 140, 93
See application file for complete search history.

(56) References Cited

U.S. PATENT DOCUMENTS

| 6,604,527 | B1 | 8/2003 | Palmisano | 128/848 |
| 6,983,752 | B2 | 1/2006 | Garabadian | 128/848 |
| 7,451,767 | B2 | 11/2008 | Keropian | 128/848 |
| 7,637,262 | B2 | 12/2009 | Bailey | 128/848 |
| 8,881,733 | B1* | 11/2014 | Harkins | 128/848 |
| 2009/0178684 | A1* | 7/2009 | Greenburg | 128/848 |
| 2010/0043805 | A1* | 2/2010 | Kelly | 128/848 |
| 2011/0017220 | A1* | 1/2011 | Lindsay et al. | 128/848 |
| 2011/0220125 | A1* | 9/2011 | Van Dyke et al. | 128/848 |

OTHER PUBLICATIONS

Davis Dental Laboratory brochure (2 pgs).
SomnoDent MAS Product Guide, downloaded from www.somnomed.com on Oct. 13, 2010 (4 pgs).
Office Action issued in related U.S. Appl. No. 13/468,766, dated Mar. 31, 2014 (24 pgs).
Notice of Allowance issued in related U.S. Appl. No. 13/468,766, dated Jul. 16, 2014 (7 pgs).

* cited by examiner

*Primary Examiner* — Victoria J Hicks
*Assistant Examiner* — Kari Petrik
(74) *Attorney, Agent, or Firm* — Hayes Soloway P.C.

(57) ABSTRACT

A mandibular advancement device used in the management of snoring, obstructive sleep apnea, TMD and bruxism and jaw clenching, comprises a maxillary tray for receiving/retaining maxillary teeth, a mandibular tray for receiving/retaining mandibular teeth, and one to two advancement member(s)/prong(s) located on the mandibular tray at the anterior region thereof. The advancement member(s)/prong(s), when in use, contact the outer surface of the maxillary tray in an anterior region thereof, thereby advancing and retaining the mandible and tongue in a protrusive position. Raized occlusal surfaces/bite pads in a region contiguous and posterior to the advancement prong(s) allow a passive tongue retaining gap or space to be formed in the anterior and posterior regions of the device. A lingual retaining strap may be provided between opposite posterior portions of the mandibular tray to passively retain the tongue in a protruded, non-obstructive position.

7 Claims, 8 Drawing Sheets

MANDIBULAR ADVANCEMENT DEVICE

CROSS REFERENCE TO RELATED APPLICATION

This application is a Continuation-in-Part of my co-pending application Ser. No. 13/468,766, filed May 10, 2012, which application in turn claims priority from U.S. Provisional Application Ser. No. 61/487,588, filed May 18, 2011, the entire disclosure of which is incorporated herein by reference.

FIELD OF THE INVENTION

The present invention relates to a mandibular advancement device, in particular, a mandibular advancement device that is simpler in design than those known in the field, and that is capable of retaining the tongue in a non-obstructive position. The invention has particular utility for treating and alleviating symptoms associated with snoring, obstructive sleep apnea, bruxism and temporomandibular joint disorders, and will be described in connection with such utility, although other utilities are contemplated.

BACKGROUND OF THE INVENTION

It is well known that snoring and obstructive sleep apnea are typically caused by a partial or complete obstruction of the pharyngeal airway during sleep. Mandibular advancement devices advance the mandible forward and consequently reduce the likelihood of the tongue and pharyngeal tissues from restricting the airway.

A number of mandibular advancement oral appliances have been proposed in the prior art. For example, U.S. Pat. No. 6,983,752, issued to Garabadian, discloses a mandibular advancement device that includes bite pads on maxillary and mandibular trays. The bite pads are located in a posterior portion of the device. The bite pads on the mandibular tray are located anterior to the bite pads of the maxillary tray. As such, when the user bites down, the mandible is extended outward due to the placement of the bite pads. That is, the anterior bite pads on the mandibular tray are held forward by the contact with the posterior bite pads on the maxillary tray. This device thus requires bite pads on both the mandibular and the maxillary trays in order to advance the mandible to the desired position.

U.S. Pat. No. 7,637,262 to Bailey discloses an oral appliance having features similar to those disclosed by Garabadian, and further includes the feature that the bite pads may form a guide plane for advancing the mandibular tray along the guide plane upon vertical closure between the trays.

Similarly, U.S. Pat. No. 6,604,527 to Palmisano discloses a mandibular advancement device that requires engaging members on both the mandibular and maxillary trays to advance the mandible. Palmisano's device includes lower flanges on a lower plate which have a trailing edge that engages with a leading edge of an upper flange that is disposed on an upper plate. The flanges are all located in a posterior portion of the device. The positioning of the flanges causes the mandible to be advanced when the device is used.

Because the Garabadian, Bailey and Palmisano devices require engaging members (e.g., bite pads, flanges, etc.) on both an upper and a lower tray, the devices can be cumbersome and awkward for a patient to wear, particularly for a full night's sleep and may cause dental/muscle/TMJ pain if the patient bruxes/clenches the teeth. Moreover, the fact that at least four engaging members are required in these devices increases the complexity of the device and increases the likelihood of failure of the device due to the failure of any individual engaging member. If the patient's mouth drops open during sleep, especially in the deeper stages of sleep (stages N3 and REM), the bite pads or guide members can disengage and allow the mandible and tongue to fall back into the oropharynx, obstructing the airway.

U.S. Pat. No. 7,451,767 to Keropian discloses an oral appliance that includes a "transpalatal bar" which extends across the posterior region of the appliance and acts as a tongue depressor to open the air passage. Posterior projections/extensions may be formed on the transpalatal bar, which hold the tongue down even further to further open the airway. However, Keropian's "transpalatal bar" is located on the underside of the appliance which is fitted to the palate and covers the upper teeth. Thus, the bar is located no lower (lingual side) than the occlusal surface of the posterior maxillary teeth. As such, the extent of tongue depression provided by the transpalatal bar is limited and can create problems if extended further down into the oropharynx. There is a problem with this design activating the gag reflex, which may not be well tolerated by many patients. This prior art appliance requires multiple follow up office visits to extend the "transpalatal bar" down the posterior aspect of the tongue to hold it forward. Regurgitation of stomach acid/digestive enzymes is also a problem while sleeping as this design does not allow the patient to swallow normally, preventing the tongue from creating a pharyngeal seal, resulting in a "reverse swallow" when in the mouth. This results in a negative esophageal pressure (partial vacuum) to develop in the esophagus and pharynx, causing the gastric contents to be "sucked up" from the stomach into the esophagus, pharynx, oral, nasal, and sinus cavities. This could be described as a form of "Iatrogenic" Gastric Esophageal Reflux Disorder (GERD), which has significant morbidity and even mortality as a long-term outcome.

Thus, there is a need in the field for a mandibular advancement oral appliance that can treat or alleviate symptoms caused by snoring and obstructive sleep apnea by advancing the mandible with a simpler device that requires fewer engagement members than required in the prior art. Furthermore, there is a need in the field for an oral appliance that can advance the mandible and retain the patient's tongue in a non-obstructive forward position when the tongue and pharyngeal muscles relax during the deepest stages of sleep, without significant side effects such as GERD.

SUMMARY OF THE INVENTION

The present disclosure is directed to a mandibular advancement device that overcomes the aforesaid and other disadvantages of the prior art. More particularly, the present disclosure provides a mandibular advancement device that includes a maxillary tray and a mandibular tray, and the mandibular tray has one to two advancement members that, when in use, protrude over an outer surface of the maxillary tray, thereby advancing the user's mandible and opening the airway.

In one aspect, the present disclosure provides a mandibular advancement device that includes a maxillary tray for receiving maxillary teeth, a mandibular tray for receiving mandibular teeth, and one to two advancement members/prongs located on the mandibular tray in an anterior region thereof. The advancement member(s)/prong(s), when in use, contact the outer surface of the maxillary tray in an anterior region thereof, thereby advancing and retaining the mandible. The advancement member(s)/prong(s) can be modified to further protrude or retrude the mandible by adding or subtracting orthodontic acrylic from the articulating surfaces (posterior surface of the advancement member(s)/prong(s) on the mandibular appliance and/or the anterior surface of the maxillary appliance). Cold cure or light activated orthodontic acrylic can be utilized for this purpose. The advancement member(s)/prong(s) may be fabricated from thermoplastic dental/orthodontic hard acrylic, plastics, thermoplastics or other polymeric material. The advancement prong(s) can also be fabricated from stainless steel dental/orthodontic wire (0.035-0.051 inch diameter) which is bent into a rectangular or elliptical shaped loop(s), then bonded and embedded into the acrylic, extending from the anterior flange back into the posterior bite pads of the mandibular tray. The preferred material is a dental/orthodontic hard acrylic or semi-soft thermoplastic plastic. When heated, using a small hand-held dental lab alcohol torch, the member(s)/prong(s) may be reshaped (tipped forward or backward). After air or water cooling, the advancement member(s)/prong(s) harden and will then hold the mandible in the more protruded or retruded position. If orthodontic wire is used to fabricate the advancement member(s)/prong(s), the member(s)/prong(s) can be bent backward or forward to further protrude or retrude the mandible when the member(s)/prong(s) of the mandibular tray contact the anterior flange of the maxillary tray when inserted in the mouth. The addition or reduction of acrylic to or from the anterior flange of the maxillary tray or tipping/reshaping of the advancement prong(s), allows titration of the appliances in the anterior-posterior dimension.

Alternatively, in other aspect of the invention, the two lateral (anterior) prongs on the mandibular tray would be replaced by a single prong located at the midline (anterior) of the lower i.e. mandibular tray.

Also, another alternative embodiment, the advancement member or members, i.e. the advancement prong or prongs may be formed of acrylic.

The mandibular tray includes two or more raised occlusal surfaces (vertical opening pads) in a region posterior to the advancement(s), allowing a gap or open space to be created large enough for a user's tongue to remain forward, when in use, between the advancement member(s)/prong(s) in the most anterior region of the device and posterior of the member(s)/prong(s) to prevent the tongue from being forced back, into the pharynx, when the jaw is closed during sleep.

The advancement member(s)/prong(s) are bonded/embedded into the mandibular tray acrylic at a region ranging from the distal aspect of the user's mandibular canines, extending posterior to the distal aspects of the second molars when in use. The exact location of the advancement member(s)/prong(s) within this range would depend on the size of the tongue and the amount of mandibular anterior repositioning desired.

The maxillary tray and the mandibular tray should be precisely fabricated/molded to conform to a user's teeth and soft tissues with no pressure or discomfort. Alternatively, a maxillary tray and the mandibular tray may be formed of a softer, "bite and boil" thermoplastic acrylic that can be fitted by the patient, similar to athletic bite guards.

In a further aspect, a flexible (elastic) strap may be disposed between the two posterior aspects (right and left sides) of the mandibular tray, and the strap should be configured to lie passively over the superior posterior (dorsal) surface of a user's tongue when in use.

The lingual strap should include a 3-5 mm thick pad, fabricated from orthodontic soft bit guard material coupled to a length of orthodontic elastic power chain or dental wire that is connected between the two sides of the most posterior aspects of the mandibular tray.

Optionally, elastic bands also may be attached between the maxillary tray and the mandibular tray, on the right and left sides in an anterior region thereof, preventing the jaws from dropping open and the appliances from disengaging during sleep.

Accordingly, an advantage of the present disclosure is to provide a mandibular advancement device that can treat or alleviate symptoms caused by snoring and obstructive sleep apnea by advancing the mandible and opening the vertical space between the dental arches during sleep with a simpler device that requires fewer engagement members than required in the prior art. The advancement member(s)/prong(s), attached to the anterior aspects of the mandibular tray, should be long enough vertically to hold the mandible and tongue in the desired anterior position, maintaining a patent oropharyngeal airway, even if the mouth opens during the deeper stages of sleep, or if the user is "mouth breathing". Furthermore, an advantage of the present disclosure is to provide a tongue retainer to further hold the tongue in a less obstructive protruded position and prevent it from falling back, blocking the airway during sleep, without creating a reverse swallow and GERD.

The features, functions and advantages that have been discussed can be achieved independently in various embodiments of the present disclosure or may be combined in yet other embodiments, further details of which can be seen with reference to the following descriptions and drawings.

BRIEF DESCRIPTION OF THE DRAWINGS

Further features and advantages of the invention will be seen from the following detailed description, taken in conjunction with the accompanying drawings, wherein like numerals depict like parts, and wherein.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

In a normal bite position, the mandibular teeth are generally located slightly posterior to the corresponding maxillary teeth. In particular, the mandibular central incisors are normally located slightly posterior to the maxillary central incisors. For mandibular advancement, it is generally desirable to advance the mandible, i.e. protrude/extend the mandible outward, preferably 50-70% of maximum mandibular protrusion. The mandibular incisors would then be advanced anterior to the maxillary incisors.

Figure 1:
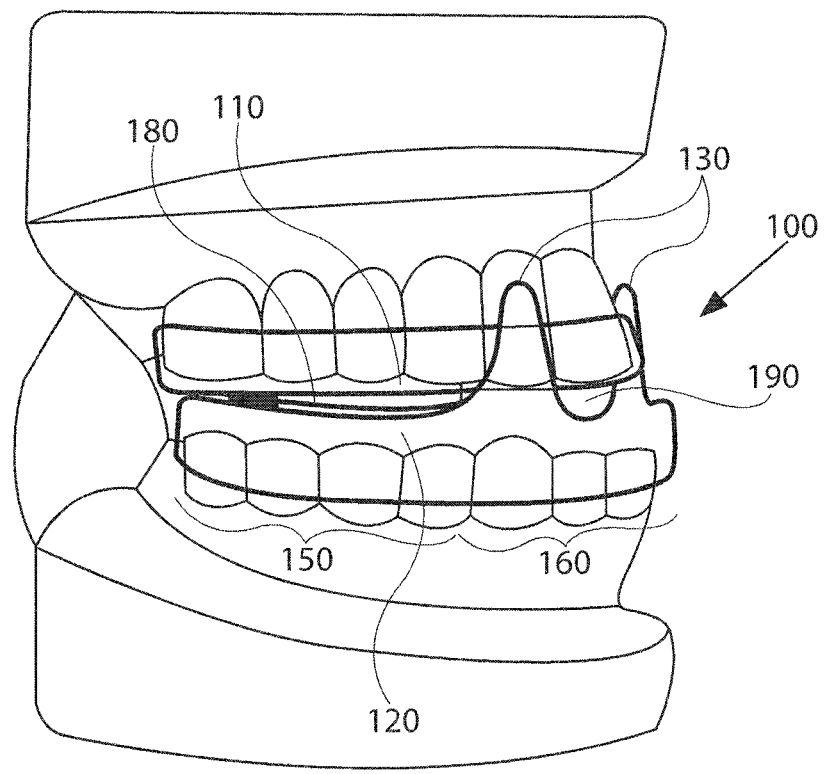
FIG. 1 illustrates a mandibular advancement device in accordance with an embodiment of the present disclosure.

FIG. 1 schematically illustrates a primary example of a mandibular advancement device provided by the present disclosure. The device 100 includes a maxillary tray 110 adapted for receiving and retaining a user's maxillary teeth, and a mandibular tray 120 for receiving and retaining the mandibular teeth. The maxillary tray 110 fits over all of the maxillary teeth of a user, while the mandibular tray 120 fits over all of the mandibular teeth of a user. The maxillary tray 110 and the mandibular tray 120 both have an anterior portion 160 which receives the anterior teeth of the user, and a posterior portion 150 which receives the posterior teeth.

The trays 110, 120 can be formed from orthodontic materials such as, for example, cold or heat cure acrylic, plastics, thermoplastics or other such polymeric material, or any other acceptable materials. The maxillary tray 110 and mandibular tray 120 preferably are custom fabricated to conform to a patient's teeth. The trays 110, 120 may be fitted to conform to the user's teeth by known manual monomer-polymer mixing/molding, heat molding and/or injection molding techniques. In one embodiment, the trays 110, 120 are of the "vaccuform" variety, i.e. the trays are made of a thermoplastic material such as a vinyl orthodontic acrylic which softens when heated. As such, the trays 110, 120 may be heated and pressure molded over the patient's plaster dental casts, thereby custom molding the trays 110, 120 to the shape of his/her maxillary and mandibular dentitions.

The mandibular tray 120 includes two advancement members or prongs 130 that protrude upward from an anterior portion 160 of the mandibular tray. Preferably, the advancement prongs 130 protrude upward from a region between about the distal aspect of the mandibular canines to about the distal aspect of the mandibular second molars. More preferably, the advancement members/prongs 130 protrude upward from the distal aspect of the mandibular canine region.

When placed in a person's mouth, the advancement members/prongs 130 on the mandibular tray 120 protrude upward such that the posterior surface of the prongs 130 contacts an outer anterior surface of the maxillary tray 110 in an anterior region 160, e.g., over about the mesial aspect of the maxillary canines to the distal aspect of the maxillary first premolars when the person closes his/her mouth. The resulting contact between the protruding members 130 on the mandibular tray 120 and the outer surface of the maxillary tray 110 positions and retains the mandible in an outwardly extended/protruded position, thereby causing the airway to open and to remain open/forward.

The mandibular tray 120 has raised occlusal surfaces (pads) 180 in a region posterior to the advancement members/prongs 130. The raised occlusal pads prevent the maxilla and mandible from over-closing, increasing the volume of the oral and pharyngeal cavities. The vertical occlusal pads can be increased or decreased in height as indicated to further increase the airway space. The occlusal pads can be modified to intentionally alter the position of the TMJ condyles (balls) within the fossae (sockets), reducing mechanical loading (compression) inside the TMJs if the patient is a jaw clencher or bruxer. The occlusal pads also prevent the muscles of mastication from over-closing, preventing jaw tendon/muscle pain. When the raised occlusal pads are optimally established, TMD and jaw muscle symptoms are significantly reduced and in most cases eliminated. Thus, when the user positions the maxillary tray 110 and mandibular tray 120 over the maxillary and mandibular dentitions, respectively, and closes/bites down, the raised surface (vertical bite pads) 180 in the region posterior to the protruding members 130, the mandibular tray occludes with the corresponding region of the maxillary tray 110. A lingual or tongue space 190, i.e. a gap or empty space, is formed in the region between the protruding members 130. The lingual space 190 provides space for the user to passively retain his/her tongue, thereby further allowing the user's tongue to position forward and anterior to the pharyngeal airway. If this tongue space is not maintained when the jaw is closed during sleep, the tongue will be forced back, into the pharyngeal airway space, contributing to airway obstruction.

Figure 2:
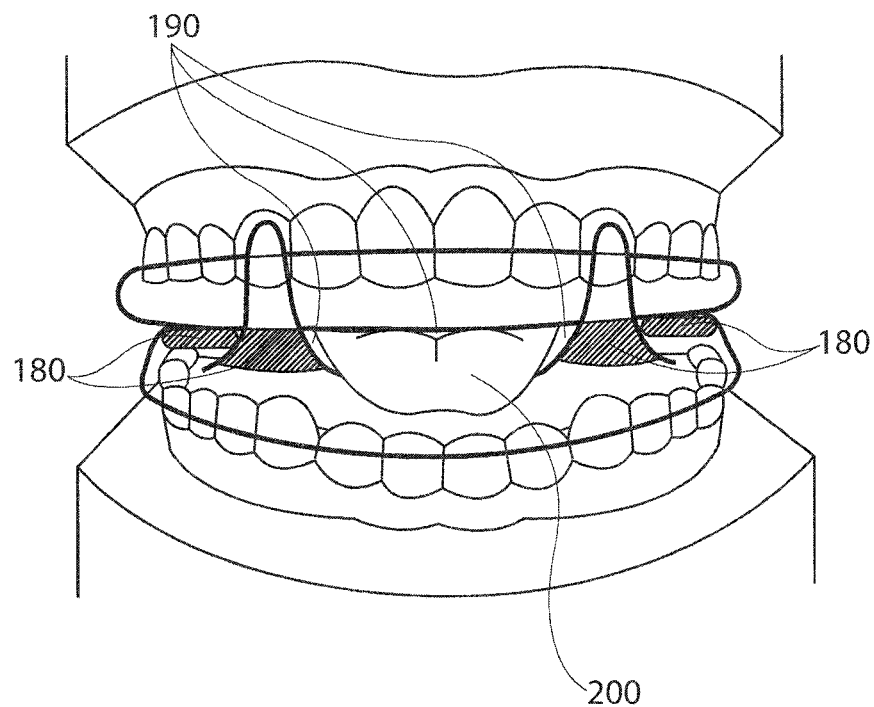
FIG. 2 illustrates a front view of the mandibular advancement device of FIG. 1.

As can be seen from a front view of the mandibular advancement device, illustrated by FIG. 2, the tongue 200 may be extended as the wearer closes/bites down, and the tongue will fit in the space provided by the lingual space 190. With the tongue so positioned, the tongue can be retained in the lingual space 190 and passively held forward of the pharyngeal airway during sleep.

Figure 3A:
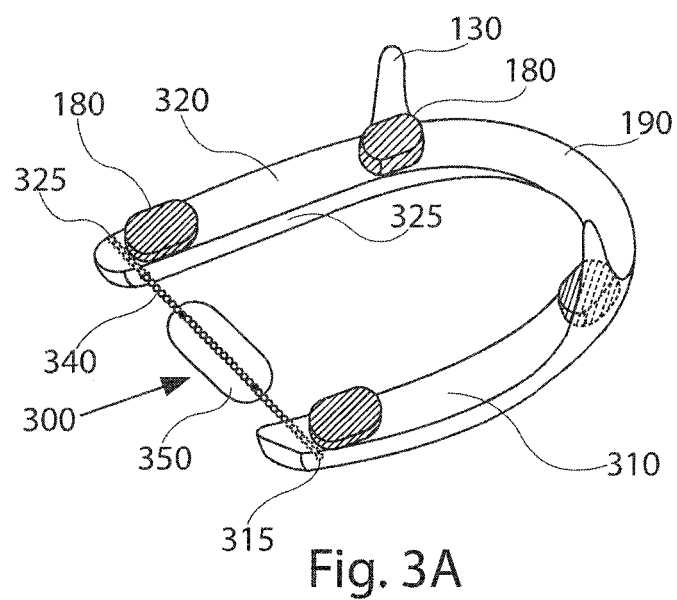
FIGS. 3A and 3B illustrates a mandibular advancement device in accordance with yet other alternative designs of a mandibular advancement (wire loop advancement prongs) in accordance with the present disclosure.

In one embodiment shown in FIG. 3A, a lingual strap 300 may be provided with the mandibular advancement device 100. The lingual strap 300 is disposed between the right and left posterior portions 310, 320 of the mandibular tray 120. For example, the lingual strap 300 may be connected between the buccal (outside) surface 315 of the mandibular tray and the contralateral buccal surface 325 of the mandibular tray. In use, the lingual strap 300 is placed over the superior posterior (dorsal) surface of the patient's tongue, thereby further holding/retaining the tongue in place or forward and reducing or preventing pharyngeal airway obstruction related to the tongue falling back during deep sleep. The lingual strap 300 may be composed of any suitable materials. For example, the lingual strap 300 may be made of elastic orthodontic power chain 340, or flexible orthodontic/dental wire 340A (FIGS. 4A and 4B, described below), attaching to the posterior sides of the mandibular tray on the buccal flange in the second molar area, and a different orthodontic material (3-5 mm thick flexible bite guard material) 350, which forms a retention pad for the tongue, connected to the power chain 340 or orthodontic/dental wire 340A for contacting the superior posterior (dorsal) surface of the tongue, retaining the tongue in a more forward, protruded position when it relaxes. The underside of the tongue retaining pad may be irregular or rough to increase the retention of the tongue. Biocompatible or dental/denture adhesives can also be applied to the tongue side of the tongue retention pad to further increase tongue retention.

Figure 3B:
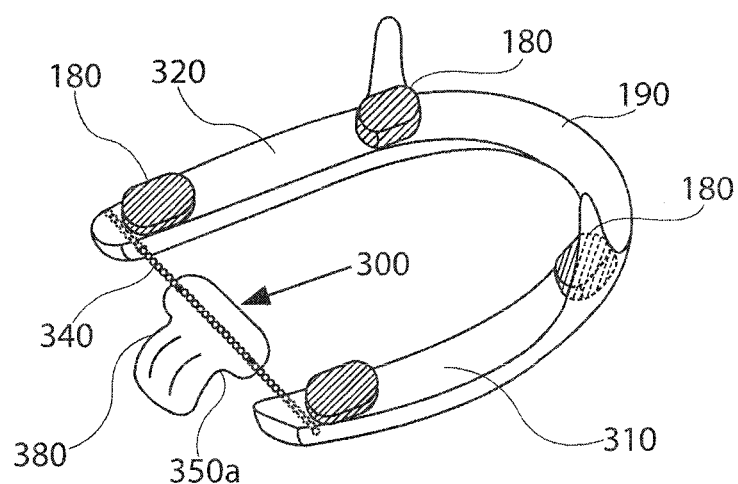

In yet another embodiment, shown in FIG. 3B, a downwardly curved extension 380 is provided on the tongue retaining pad 350a for engaging with the distal end of the wearer's tongue. The tongue must be allowed to seal off the oral-velopharynx when the patient swallows during sleep. The orthodontic power chain material or orthodontic/dental wire used to hold the tongue retention pad must be elastic and/or flexible enough to allow the dorsal aspect of the tongue to position up and back during swallowing, preventing choking or drooling from saliva buildup, and/or gastric regurgitation (GERD).

Figure 4A:
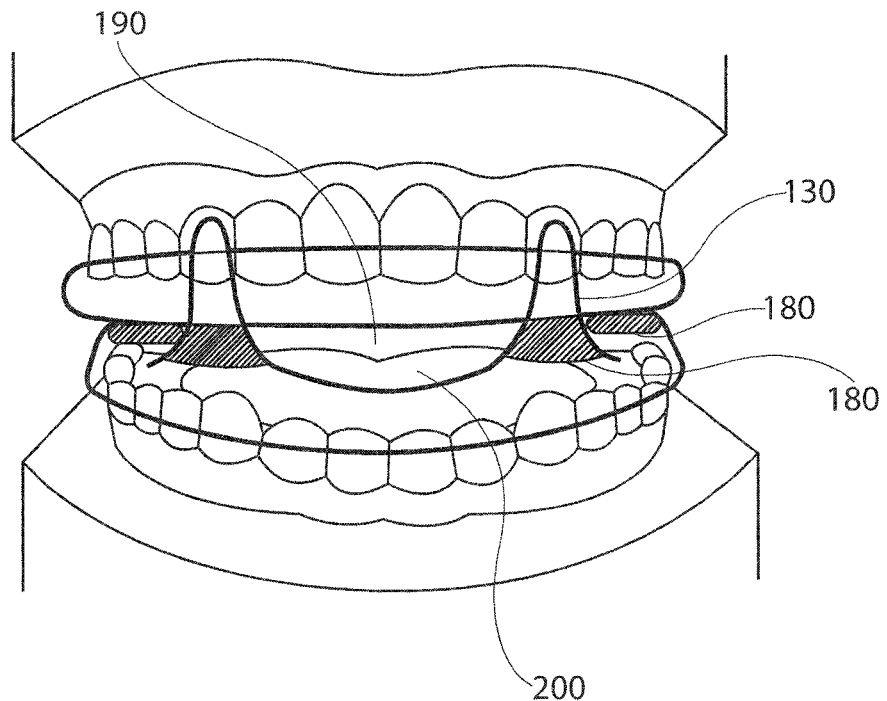
FIGS. 4A and 4B are views similar to FIGS. 2 and 3B, respectively, of a mandibular advancement device in accordance with yet a further embodiment of the present disclosure.
Figure 4B:
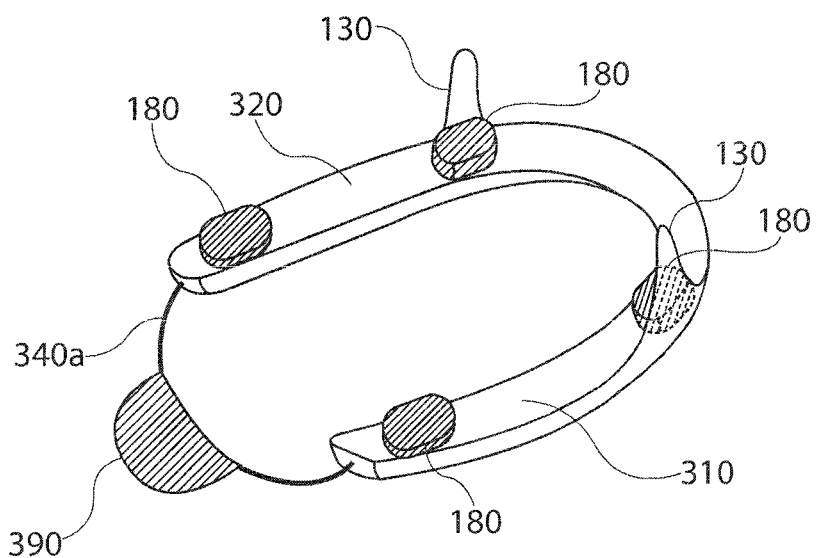
Figure 5A:
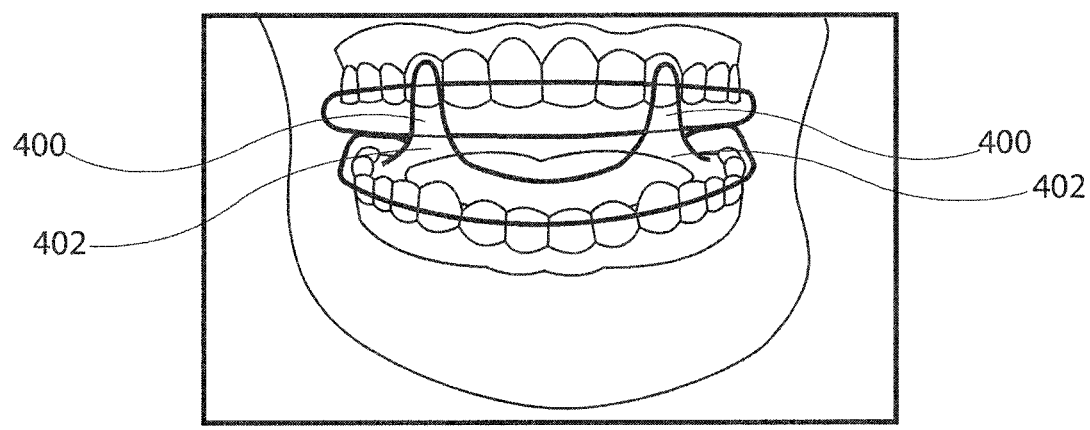
FIGS. 5A and 5B are views similar to FIGS. 1 and 2 of a mandibular advancement device in accordance with still yet another embodiment of the invention.
Figure 5B:
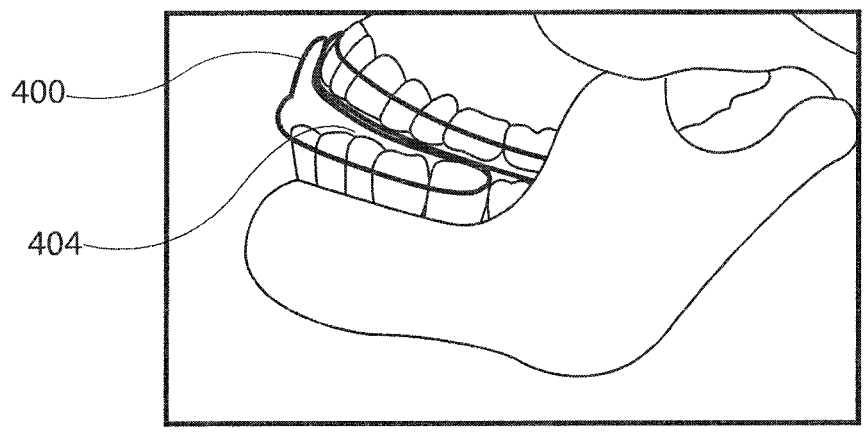

In yet another embodiment, illustrated in FIGS. 4A and 4B, the lingual strap is formed of flexible orthodontic/dental wire 340A. A downwardly curved extension 390, similar to extension 380 shown in FIG. 3B, is provided for engaging with the distal end of the wearer's tongue. In still yet another embodiment of the invention, illustrated in FIGS. 5A and 5B of the advancement members or prongs 400 are integrally formed, e.g. of acrylic and protrude upwardly from an anterior portion 402 of the mandibular tray 404. As before, the advancement prongs protrude upwards from a region between about the distal aspect of the mandibular canines to about the distal aspect of the mandibular first premolars. More preferably, the advancement member/prongs protrude upward from the distal aspect of the mandibular canine-premolar region.

Figure 6A:
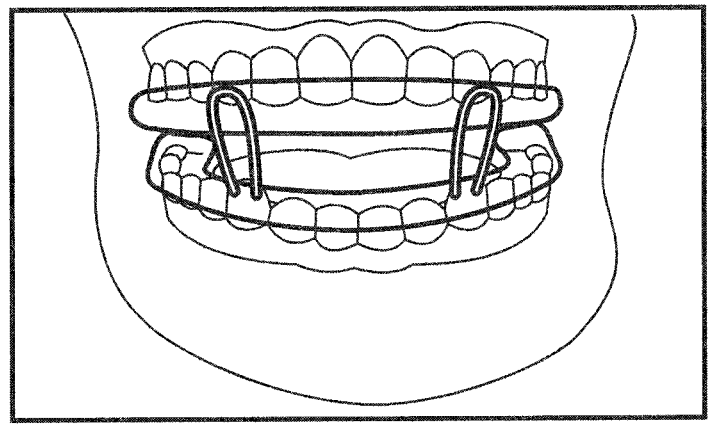
FIGS. 6A and 6B are views similar to FIGS. 1 and 2 of still yet another embodiment of the invention.
Figure 6B:
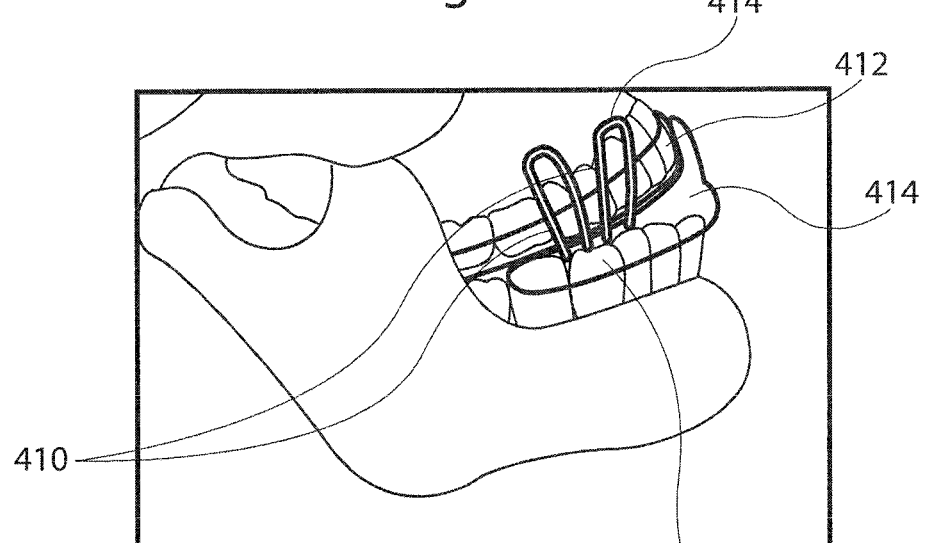

Still yet another embodiment of the invention is shown in FIGS. 6A and 6B. In this embodiment, elastic bands 410 are fixed between the maxillary tray 412 and mandibular tray 414 on fixtures 414, 416 extending outward from the maxillary and the mandibular trays. The fixtures 414, 416 are located adjacent of the advancement members or prongs of the region between the advancement member/prong and the posterior portion of the trays, i.e. adjacent the premolar or molar region.

Figure 7A:
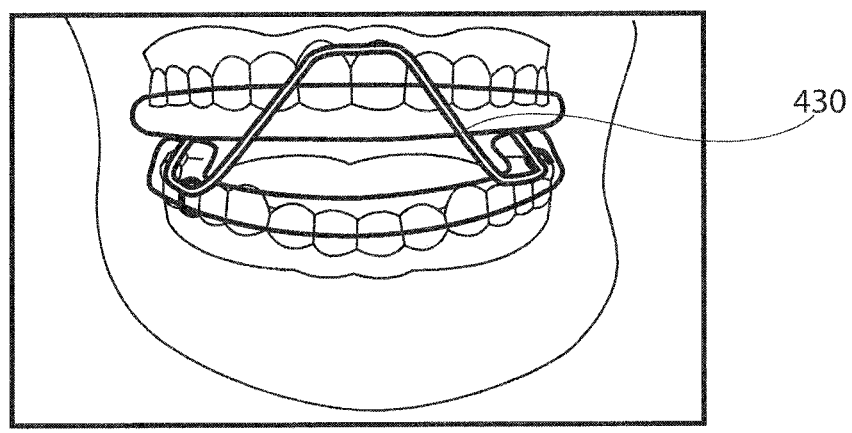
FIGS. 7A and 7B are view similar to FIGS. 1 and 2 of still yet a further embodiment of the invention.
Figure 7B:
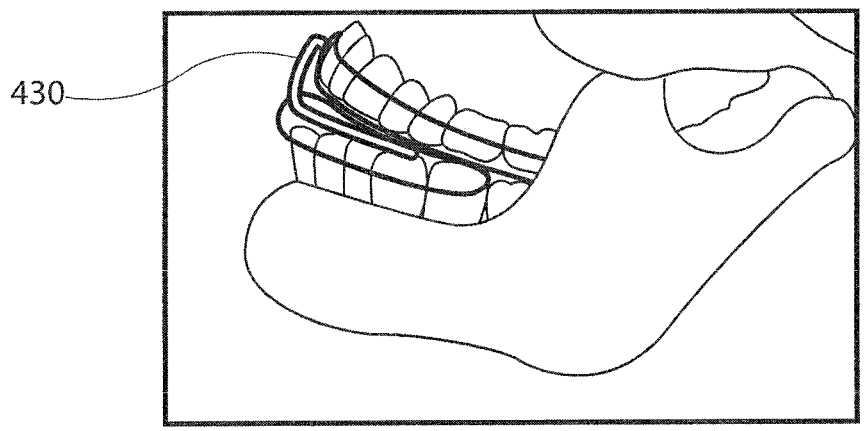

Referring to FIGS. 7A and 7B in yet another embodiment of the invention, the advancement member/prongs of the previously discussed embodiments, are replaced by a single prong 430, located at the midline (anterior) of the lower appliance. Everything else remains the same.

Figure 8:
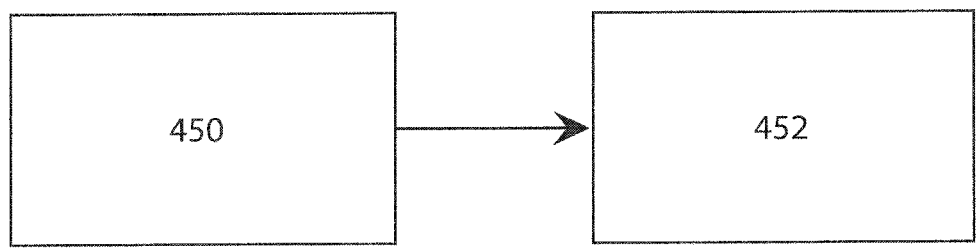
FIG. 8 is a block diagram showing yet another embodiment of the invention.

Referring to FIG. 8, in still yet another embodiment of the invention, the maxillary tray and the mandibular tray both are prefabricated, with a single advancement prong or pair of advancement prongs formed of wire, and embedded in a relatively soft thermoplastic acrylic. The maxillary tray and mandibular tray have been fitted to a patient, similar to athletic bite guards of the like, in a step 450. The soft thermoplastic acrylic forms to the patients teeth. The formed maxillary tray and mandibular tray are then placed in boiling water in a fixing step 452 thereupon the thermoplastic acrylic hardens in the shape of the wearer's bite.

Heat cure, cold cure or UV light activated orthodontic/dental acrylic can be added to or removed from the articulating surfaces of the maxillary or mandibular trays by the dentist or dental technician on follow up visits to titrate the appliance (further protrude or retrude, increase or decrease the vertical dimension of the mandibular tray) as indicated.

The mandibular advancement device provided by the present disclosure, by causing the mandible to be protruded and separated vertically from the maxilla, allows the tongue to remain forward/protruded during sleep, preventing it from being forced back or collapsing back into the airway, and thereby holding open the pharyngeal airway during sleep. This prevents snoring and obstructive sleep apnea. Because the tongue is attached to the mandible along the floor of the mouth, retaining the mandible forward and more open, will simultaneously retain the tongue in a more protruded-open position with the attached mandible. With this appliance design and tongue retention strap, the appliance is more effective in treating more severe cases of obstructive sleep apnea than appliance prior designs.

Moreover, the mandibular advancement device can alleviate or treat Temporomandibular Joint Dysfunction (TMD), which may be related to bruxism or clenching, jaw muscle and tendon pain, TMJ ligament/disc problems and/or pre-existing TMJ arthritis among other potential causes, because use of the device reduces the mechanical loading of the jaw joints (TMJs) if the user grinds (bruxes) or clenches his/her teeth during sleep. It can also prevent the backward displacement of the mandible during sleep which allows compression of the neurovascular tissue located in the superio-posterior aspect of the TMJ fossa. In addition, the device can reduce/prevent muscle pain/spasms from over-closed jaws related to teeth/jaw clenching by establishing posterior contact between the maxillary and mandibular trays in an increased vertical (open) position, compared to the tooth to tooth contact during sleep of a bruxism, jaw clenching and/or TMD patient.

Retaining the tongue and mandible in a protrusive/open position during sleep also appears to reduce nocturnal jaw/tooth clenching and significantly reduce the amount of mechanical force related to jaw muscle contraction compared to a more posterior jaw position.

Various changes may be made in the invention without departing from the spirit and the scope thereof. It should be emphasized that the above-described embodiments of the present mandibular advancement device are merely possible examples of implementations and are merely set forth for a clear understanding of the principles of the invention. Many different embodiments of the mandibular advancement device described herein may be designed and/or fabricated without departing from the spirit and scope of the invention. All these and other such modifications and variations are intended to be included herein within the scope of this disclosure and protected by the following claims. Therefore the scope of the invention is not intended to be limited except as indicated in the appended claims.

What is claimed is:

1. A mandibular advancement device comprising:
   a maxillary appliance for receiving and retaining maxillary teeth;
   a mandibular appliance for receiving and retaining mandibular teeth;
   at least one advancement prong, located at the anterior of said mandibular appliance, wherein said at least one advancement prong, when in use, contacts an outer surface of the maxillary appliance in an anterior region thereof, thereby advancing and retaining a wearer's mandible forward;
   a tongue strap in the form of a flexible elastic strap or a wire disposed between two most distal aspects of opposing portions of the mandibular appliance, wherein said strap or wire is configured to lie over a superior posterior or dorsal surface of the wearer's tongue when in use, wherein the tongue strap comprises a length of orthodontic elastic power chain or a flexible dental wire, and wherein the elastic power chain or flexible dental wire has a flexible tongue retaining pad that is connected between the opposing portions of the mandibular appliance by the elastic power chain or flexible dental wire; and
   elastic bands attached between the maxillary appliance and the mandibular appliance on opposite sides on an anterior region thereof.

2. The device of claim 1, wherein the at least one advancement prong comprises a vertically extending projection.

3. The device of claim 1, wherein the mandibular appliance also includes two raised occlusal bite pads in a region posterior to the at least one advancement prong.

4. The device of claim 3, further comprising two additional raised occlusal bite pads located adjacent to a most posterior aspect of the mandibular appliance, to prevent compression of the wearer's temporomandibular joint, shortening of the wearer's jaw closing muscles and reduced mechanical tension on the wearer's jaw muscle tendons when the device is in use.

5. The device of claim 3, wherein an anterior lingual gap for passively retaining the wearer's tongue is formed between the at least one advancement prong and the posterior occlusal bite pads of the mandibular advancement device when in use.

6. The device of claim 1, wherein the maxillary appliance and the mandibular appliance are formed of a "boil and bite" thermoplastic acrylic.

7. The device of claim 1, wherein the maxillary appliance and the mandibular appliance are custom fabricated to conform to the wearer's teeth.

* * * * *